US012766136B2

(12) United States Patent
Kupferman et al.

(10) Patent No.: US 12,766,136 B2
(45) Date of Patent: Oct. 20, 2026

(54) COMPOSITIONS FOR TREATING OR PREVENTING PAIN

(71) Applicant: Kallyope, Inc., New York, NY (US)

(72) Inventors: Justine Kupferman, New York, NY (US); Shirly Pinto, Ridgewood, NJ (US); Brett Lauring, Tenafly, NJ (US); Michael Crutchlow, Penn Valley, PA (US); Annemarie Vance, Libertyville, IL (US); Jiajun Liu, Lexington, MA (US)

(73) Assignee: KALLYOPE, INC., New York, NY (US)

( * ) Notice: Subject to any disclaimer, the term of this patent is extended or adjusted under 35 U.S.C. 154(b) by 0 days.

(21) Appl. No.: 19/364,247

(22) Filed: Oct. 21, 2025

(65) Prior Publication Data

US 2026/0108507 A1 Apr. 23, 2026

Related U.S. Application Data

(60) Provisional application No. 63/894,983, filed on Oct. 7, 2025, provisional application No. 63/710,727, filed on Oct. 23, 2024.

(51) Int. Cl.
*A61K 31/472* (2006.01)
*A61P 25/06* (2006.01)

(52) U.S. Cl.
CPC ............ *A61K 31/472* (2013.01); *A61P 25/06* (2018.01)

(58) Field of Classification Search
CPC .............................. A61K 31/472; A61P 25/06
See application file for complete search history.

(56) References Cited

U.S. PATENT DOCUMENTS

| | | | | |
|---|---|---|---|---|
| 9,487,488 | B2 * | 11/2016 | Kato | C07D 217/22 |
| 9,540,360 | B2 * | 1/2017 | Tsuzuki | A61P 13/08 |
| 10,993,939 | B2 * | 5/2021 | Palumbo | A61K 31/4725 |
| 12,281,114 | B2 | 4/2025 | He et al. | |
| 2021/0177830 | A1 * | 6/2021 | Palumbo | A61K 31/4725 |

FOREIGN PATENT DOCUMENTS

| | | | |
|---|---|---|---|
| EP | 2896613 | A1 | 7/2015 |
| JP | 2014074021 | A | 4/2014 |
| JP | 2018062513 | A | 4/2018 |
| JP | 2019116445 | A | 7/2019 |
| WO | WO-2012120398 | A1 | 9/2012 |
| WO | WO2012124825 | * | 9/2012 |
| WO | WO-2012124825 | A1 | 9/2012 |
| WO | WO-2012177893 | A2 | 12/2012 |
| WO | WO2017217351 | * | 12/2017 |
| WO | WO-2023211779 | A1 | 11/2023 |
| WO | WO-2024220539 | A1 | 10/2024 |
| WO | WO-2025064492 | A1 | 3/2025 |
| WO | WO-2026090164 | A1 | 4/2026 |
| WO | WO-2026090165 | A1 | 4/2026 |

OTHER PUBLICATIONS

Abe, Junji et al. Ca2+-dependent PKC activation mediates menthol-induced desensitization of transient receptor potential M8. Neuroscience Letters 397(1-2):140-144 (2006).

Burgos-Vega, Carolina C. et al. Meningeal transient receptor potential channel M8 activation causes cutaneous facial and hindpaw allodynia in a preclinical rodent model of headache. Cephalalgia : an international journal of headache 36(2):185-193 (2016). Published Online May 5, 2015.

Chaplan, Sandra R. et al. Quantitative Assessment of Tactile Allodynia in the Rat Paw. Journal of Neuroscience Methods 53(1):55-63 (1994).

Dallel, Radhouane et al. Recurrent administration of the nitric oxide donor, isosorbide dinitrate, induces a persistent cephalic cutaneous hypersensitivity: A model for migraine progression. Cephalalgia : an international journal of headache 38(4):776-785 (2018). Published Online May 31, 2017.

Dussor, Greg et al. TRPM8 and Migraine. Headache 56(9):1406-1417 (2016).

Ernstsen, Charlotte et al. No additive effect of combining sumatriptan and olcegepant in the GTN mouse model of migraine. Cephalalgia : an international journal of headache 41(3):329-339 (2021). Published Online Oct. 15, 2020.

Fernndez-Carvajal, Asia et al. Investigational drugs in early phase clinical trials targeting thermotransient receptor potential (thermoTRP) channels. Expert opinion on investigational drugs 29(11):1209-1222 (2020).

Ferrari, M.D. et al. Oral triptans (serotonin 5-HT(1B/1D) agonists) in acute migraine treatment: a meta-analysis of 53 trials. Lancet 358(9294):1668-1675 (2001).

Horne, Daniel B. et al. Discovery of TRPM8 Antagonist ( S)-6-(((3-Fluoro-4-(trifluoromethoxy)phenyl)(3-fluoropyridin-2-yl)methyl)carbamoyl)nicotinic Acid (AMG 333), a Clinical Candidate for the Treatment of Migraine. Journal of medicinal chemistry 61(18):8186-8201 (2018).

Karsan, Nazia et al. Headache and non-headache symptoms provoked by nitroglycerin in migraineurs: A human pharmacological triggering study. Cephalalgia : an international journal of headache 40(8):828-841 (2020).

Martin-Escura, Cristina et al. Beta-Lactam TRPM8 Antagonist RGM8-51 Displays Antinociceptive Activity in Different Animal ModelsInternational journal of molecular sciences 23(5):2692, 1-24 (2022).

McKemy, David D. et al. Identification of a cold receptor reveals a general role for TRP channels in thermosensation. Nature 416(6876):52-58 (2002).

(Continued)

*Primary Examiner* — D Margaret M Seaman
(74) *Attorney, Agent, or Firm* — WILSON SONSINI GOODRICH & ROSATI

(57) ABSTRACT

The present disclosure is directed to compositions comprising 4-({(4-cyclopropylisoquinolin-3-yl)[4-(trifluoromethoxy)benzyl]amino}sulfonyl)benzoic acid, or a pharmaceutically acceptable salt thereof, for treating or preventing pain, for example migraine, in a subject, and methods which comprises administering the said compound, or the pharmaceutically acceptable salt thereof, respectively.

13 Claims, No Drawings

(56) References Cited

OTHER PUBLICATIONS

Premkumar, Louis S. et al. Downregulation of transient receptor potential melastatin 8 by protein kinase C-mediated dephosphorylation. The Journal of Neuroscience 25(49):11322-11329 (2005).
Shiraki, Chinatsu et al. Role of TRPM8 in switching between fever and hypothermia in adult mice during endotoxin-induced inflammation. Brain, behavior, & immunity—health 16:100291, 1-17 (2021).
Sureda-Gibert, Paula et al. Nitroglycerin as a model of migraine: Clinical and preclinical review. Neurobiology of pain (Cambridge, Mass.) 12:100105, 1-12 (2022).
Weyer, Andy D. et al. Development of TRPM8 Antagonists to Treat Chronic Pain and Migraine. Pharmaceuticals (Basel, Switzerland) 10(2):37, 1-9 (2017).
Winchester, Wendy J. et al. Inhibition of TRPM8 channels reduces pain in the cold pressor test in humans. The Journal of pharmacology and experimental therapeutics 351(2):259-269 (2014).
Berge, Stephen M. et al. Pharmaceutical Salts. Journal of Pharmaceutical Sciences 66(1):1-19 (1977).
Burgos-Vega, Carolina C. et al. Meningeal transient receptor potential channel M8 activation causes cutaneous facial and hindpaw allodynia in a preclinical rodent model of headache. Cephalalgia 36(2):185-193 (2016).
ClinicalTrials.gov Identifier: NCT02675309. A Study to Investigate the Effect of MT-8554 on the Pharmacokinetics of Simvastatin and Rosuvastatin in Healthy Subjects, Record Created Mar. 24, 2016; [retrieved on Feb. 2, 2026]. Available at https://clinicaltrials.gov/study/NCT02675309 pp. 1-8.
PCT/US2025/051872 International Search Report and Written Opinion dated Jan. 8, 2026.
PCT/US2025/051873 International Search Report and Written Opinion dated Jan. 8, 2026.
Schank, J.R. GenBank Accession No. NM_001059. Version No. NM_001059.3. *Homo sapiens* tachykinin receptor 3 (TACR3), mRNA: pp. 1-5. Record created Nov. 22, 2018. Retrieved Aug. 12, 2024. Retrieved from: https://www.ncbi.nlm.nih.gov/nuccore/NM_001059.
Sureda-Gibert, Paula et al. Nitroglycerin as a Model of Migraine: Clinical and Preclinical Review. Neurobiology of pain 12:100105, 1-12 (2022).
ClinicalTrials.gov Identifier: NCT02803268. A Study to Investigate the Safety, Tolerability and Pharmacokinetics of Multiple Doses of MT-8554 in Female Subjects Experiencing Vasomotor Symptoms, Record Created Jun. 14, 2016; [retrieved on Jun. 8, 2026]. Available at URL:https://clinicaltrials.gov/study/NCT02803268 pp. 1-8.
ClinicalTrials.gov Identifier: NCT02429102. A Study to Investigate the Safety, Tolerability and Pharmacokinetics of MT-8554 in Healthy Subjects, Record Created Apr. 28, 2015; [retrieved on Jun. 8, 2026]. Available at URL: https://clinicaltrials.gov/study/NCT02429102cond=NCT02429102&viewType=Card&rank=1 pp. 1-8.
ClinicalTrials.gov Identifier: NCT02536209. A Study to Investigate the Pharmacodynamic Effect of Single Doses of MT-8554 in Healthy Subjects, Record Created Aug. 27, 2015; [retrieved on Jun. 8, 2026]. Available at URL:https://clinicaltrials.gov/study/NCT02536209 pp. 1-9.
ClinicalTrials.gov Identifier: NCT03172598. Study to Assess the Efficacy, Safety and Tolerability of MT-8554 in Subjects With Painful Diabetic Peripheral Neuropathy, Record Created May 31, 2017; [retrieved on Jun. 8, 2026]. Available at URL:https://clinicaltrials.gov/study/NCT03172598 pp. 1-8.
ClinicalTrials.gov Identifier: NCT03291067. MT-8554 for Reduction of Vasomotor Symptoms in Postmenopausal Women, Record Created Sep. 20, 2017; [retrieved on Jun. 8, 2026]. Available at URL:https://clinicaltrials.gov/study/NCT03291067 pp. 1-13.
ClinicalTrials.gov Identifier: NCT03381404. Mass Balance Study With MT-8554 (MT-8554 MB), Record Created Dec. 17, 2017; [retrieved on Jun. 8, 2026]. Available at URL:https://clinicaltrials.gov/study/NCT03381404 pp. 1-10.
ClinicalTrials.gov Identifier: NCT03471130. Definitive QT Study With MT-8554 (MT-8554 DQT), Record Created Mar. 19, 2018; [retrieved on Jun. 8, 2026]. Available at URL:https://clinicaltrials.gov/study/NCT03471130 pp. 1-10.
ClinicalTrials.gov Identifier: NCT03541200. Long-term Safety and Efficacy Study of MT-8554 in Postmenopausal Women With Vasomotor Symptoms, Record Created May 17, 2018; [retrieved on Jun. 8, 2026]. Available at URL:https://clinicaltrials.gov/study/NCT03541200 pp. 1-12.
ClinicalTrials.gov Identifier: NCT05123196. Exploratory Study of MT-8554 in Subjects With Painful Diabetic Peripheral Neuropathy, Record Created Nov. 5, 2021; [retrieved on Jun. 8, 2026]. Available at URL:https://clinicaltrials.gov/study/NCT05123196 pp. 1-13.

* cited by examiner

COMPOSITIONS FOR TREATING OR PREVENTING PAIN

CROSS-REFERENCE TO RELATED APPLICATIONS

This application claims the benefit of U.S. Provisional Application No. 63/710,727 filed Oct. 23, 2024, and U.S. Provisional Application No. 63/894,983 filed Oct. 7, 2025, each of which is hereby incorporated by reference in its entirety.

BACKGROUND OF THE INVENTION

Migraine is a painful and debilitating neurological condition of the trigeminovascular system with high prevalence in the general population, affecting approximately 15% of individuals, making it the second leading cause of disability worldwide. Migraine is characterized by recurrent, pulsating headache attacks of moderate to severe pain intensity with sensitivity to movement, visual, auditory, and other sensory input that can last from 4 to 72 hours.

While there are several classes of oral drugs approved for migraine treatment, many of those currently in use are associated with significant side effects, leading to frequent discontinuation and class switching along with poor outcomes. Small molecule triptans, which are selective serotonin 5-HT1B/ID agonists, are used to treat migraine and are generally well tolerated. However, triptans are contraindicated in cardiovascular disease, and many patients do not respond favorably to triptans. In an analysis of 53 trials, up to one third of patients with migraine and 40% of all migraine attacks did not respond to treatment with triptans (Ferrari, et al., Lancet, vol. 358:1668-1675 (2001)). Antibody therapies and small molecules targeting CGRP receptors have fewer reported side effects, but similarly less than a third of migraineurs are responsive to these treatments. Thus, there is significant need for novel therapies to treat migraine and other disorders of the trigeminovascular system such as cluster and medication overuse headache and trigeminal neuralgia.

Transient receptor potential melastatin eight (TRPM8) is a transient receptor potential channel that is expressed in trigeminal neurons and is involved in cold and menthol sensation, as well as other processes. TRPM8 has been implicated in the regulation of certain physiological processes, including cold allodynia and hyperalgesia after inflammation or nerve injury as well as migraine. Pfizer and Amgen have each progressed selective oral small molecule TRPM8 inhibitors into clinical trials for the treatment of pain and migraine (PF-05105679 and AMG 333, respectively). However, unwanted side effects, such as feeling hot, paresthesia, dysesthesia, dysgeusia, and general body temperature dysregulation led to discontinuation of the clinical trials. For example, it was found that PF-05105679 induced an unexpected adverse event (feeling hot) in 23 and 36% of volunteers (600- and 900-mg dose, respectively), and which in two volunteers was non-tolerable (J Pharmacol Exp Ther 351:259-269, November 2014). In this study, the effect of PF-05105679 in the cold pressor test and the induction of the adverse events occurred at the same doses, meaning there was no measurable therapeutic index for the compound.

Thus, there is a need for new, safe, and effective treatments for treating migraine and other trigeminal pain disorders which do not have the undesired side effects seen in current treatments.

SUMMARY OF THE INVENTION

The present disclosure provides a method for treating or preventing a migraine and other trigeminal pain disorders, comprising administering to the subject a therapeutically effective amount of the TRPM8 inhibitor 4-({(4-cyclopropylisoquinolin-3-yl)[4-(trifluoromethoxy)benzyl]amino}sulfonyl)benzoic acid (also known as elismetrep), or a pharmaceutically acceptable salt thereof. As disclosed herein, elismetrep is a TRPM8 antagonist compound which, in contrast to PF-05105679 and AMG 333, does not lead to undesired side effects at therapeutically effective doses.

In one aspect, disclosed herein is a method for treating or preventing a disease or condition in a subject in need thereof, comprising administering to the subject a therapeutically effective amount of 4-({(4-cyclopropylisoquinolin-3-yl)[4-(trifluoromethoxy)benzyl]amino}sulfonyl)benzoic acid, or a pharmaceutically acceptable salt thereof, wherein the disease or condition is migraine or a trigeminal pain disease or condition. In some embodiments, the disease or condition is selected from the group consisting of migraine, medication overuse headache, cluster headache, general headache, trigeminal neuralgia, trigeminal neuropathy, trigeminal autonomic cephalalgia, orofacial pain, and dental pain. In some embodiments, wherein the disease or condition is selected from the group consisting of migraine, medication overuse headache, cluster headache, and general headache. In some embodiments, wherein the disease or condition is migraine.

In some embodiments of the methods disclosed herein, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof, is an amount which does not induce an undesired side effect, wherein the undesired side effect comprises body temperature dysregulation, feeling hot, paresthesia, dysesthesia, dysgeusia, or a combination thereof. In some embodiments, the undesired side effect comprises feeling hot, paresthesia, dysesthesia, dysgeusia, or a combination thereof. In some embodiments, the therapeutic index of 4-({(4-cyclopropylisoquinolin-3-yl)[4-(trifluoromethoxy)benzyl]amino}sulfonyl)benzoic acid, or a pharmaceutically acceptable salt thereof, is at least 5:1, at least 10:1, at least 20:1, at least 30:1, at least 40:1, at least 50:1, at least 60:1, at least 70:1, at least 80:1, at least 90:1, at least 100:1, or more, wherein the therapeutic index is measured as the ratio of minimal dose for onset of the undesired side effect:minimum dose needed for efficacy in treating or preventing the disease or condition in an animal model.

In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof, is administered orally to the subject.

In some embodiments, the subject is a human.

In another aspect, disclosed herein is a method of treating or preventing a disease or condition in a human in need thereof, the method comprising orally administering to the human a therapeutically effective amount of 4-({(4-cyclopropylisoquinolin-3-yl)[4-(trifluoromethoxy)benzyl]amino}sulfonyl)benzoic acid, or a pharmaceutically acceptable salt thereof, wherein the disease or condition is migraine, medication overuse headache, cluster headache, general headache, trigeminal neuralgia, trigeminal neuropathy, trigeminal autonomic cephalalgia, and orofacial pain, or a combination thereof.

In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof, is an amount which provides efficacy but does not produce a severe treatment-emergent adverse event (TEAE). In some embodiments, efficacy refers to achieving pain freedom (PF), freedom from the most bothersome symptom (MBS) associated with migraine, or pain relief (PR) two hours post-dosing of elismetrep. In some embodiments, the TEAE comprises feeling hot, paresthesia, dysesthesia, dysgeusia, or a combination thereof.

In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is less than 10 mg, less than 15 mg, less than 20 mg, or less than 25 mg. In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is from 0.1 mg to 25 mg. In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is from 0.1 mg to 20 mg. In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is from 0.1 mg to 15 mg. In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is from 0.1 mg to 10 mg. In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is about 2 mg, about 5 mg, about 10 mg, or about 20 mg. In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is about 10 mg or about 20 mg. In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is about 10 mg. In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is about 20 mg.

In some embodiments, the 4-({(4-cyclopropylisoquinolin-3-yl)[4-(trifluoromethoxy)benzyl]amino}sulfonyl)benzoic acid, or a pharmaceutically acceptable salt thereof, is administered daily. In some embodiments, the 4-({(4-cyclopropylisoquinolin-3-yl)[4-(trifluoromethoxy)benzyl]amino}sulfonyl)benzoic acid, or a pharmaceutically acceptable salt thereof, is administered once or twice daily.

In some embodiments, the 4-({(4-cyclopropylisoquinolin-3-yl)[4-(trifluoromethoxy)benzyl]amino}sulfonyl)benzoic acid, or a pharmaceutically acceptable salt thereof, is administered upon sensing the onset of symptoms of the disease or condition. In some embodiments, the disease or condition is migraine.

In another aspect, disclosed herein is a method of treating or preventing migraine in a human in need thereof, the method comprising orally administering to the human a therapeutically effective amount of 4-({(4-cyclopropylisoquinolin-3-yl)[4-(trifluoromethoxy)benzyl]amino}sulfonyl)benzoic acid, or a pharmaceutically acceptable salt thereof. In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is less than 10 mg, less than 15 mg, less than 20 mg, or less than 25 mg. In some embodiments, the therapeutically effective amount is from 0.1 mg to 25 mg. In some embodiments, the therapeutically effective amount is from 0.1 mg to 20 mg. In some embodiments, the therapeutically effective amount is from 0.1 mg to 15 mg. In some embodiments, the therapeutically effective amount is from 0.1 mg to 10 mg. In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is a therapeutically effective amount of about 2 mg, about 5 mg, about 10 mg, or about 20 mg. In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is about 10 mg or about 20 mg. In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is about 10 mg. In some embodiments, the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof is about 20 mg.

In some embodiments, the 4-({(4-cyclopropylisoquinolin-3-yl)[4-(trifluoromethoxy)benzyl]amino}sulfonyl)benzoic acid, or a pharmaceutically acceptable salt thereof is administered upon sensing the onset of a migraine. In some embodiments, the 4-({(4-cyclopropylisoquinolin-3-yl)[4-(trifluoromethoxy)benzyl]amino}sulfonyl)benzoic acid, or a pharmaceutically acceptable salt thereof is administered daily.

In some embodiments, the 4-({(4-cyclopropylisoquinolin-3-yl)[4-(trifluoromethoxy)benzyl]amino}sulfonyl)benzoic acid, or a pharmaceutically acceptable salt thereof is administered once daily upon sensing the onset of a migraine.

DETAILED DESCRIPTION OF THE INVENTION

Transient receptor potential (TRP) channels are non-selective cation channels that are activated by a variety of physical (e.g., temperature, osmolarity, mechanical) and chemical stimuli. A subset of the TRP channel superfamily is thermoresponsive, each channel activated over a discrete temperature range, cumulatively spanning from noxious cold to noxious heat. TRPM8 belongs to the melastatin subgroup of the TRP channel superfamily. TRPM8 is sensitive to cold temperature and menthol, and thus is also called the cold and menthol receptor-1 (CMR-1). (McKemy et al., Nature, Vol. 416, No. 6876, pp. 52-58 (2002)). TRPM8 is known to be stimulated by cool to cold temperatures (8 to 28° C.) as well as by chemical substances such as menthol and icilin.

TRPM8 is located on primary nociceptive neurons (A-8 and C-fibers) and is also modulated by inflammation-mediated second messenger signals. (Abe et al., Neuroscience Letters, Vol. 397, No. 1-2, p. 140-144 (2006); Premkumar et al., The Journal of Neuroscience, Vol. 25, No. 49, p. 11322-11329 (2005)). TRPM8 is highly expressed in sensory neurons of the trigeminal and dorsal root ganglia. TRPM8 is also known to be expressed in the brain, lung, bladder, gastrointestinal tract, blood vessels, prostate, and immune cells. Experimental evidence implicates TRPM8 channels in cold allodynia, hyperalgesia after inflammation or nerve injury, as well as in migraine (Weyer A D, Lehto S G. Pharmaceuticals (Basel). 2017; 10:37-46).

However, despite the promising preclinical biology and physiology, each TRPM8 inhibitor that has entered the clinic has exited for undesired side effects which precluded further clinical progress. Both Pfizer's selective TRPM8 antagonist 3-[[[(1R)-1-(4-fluorophenyl)ethyl](3-quinolinylcarbonyl) amino]methyl]benzoic acid (PF-05105679) and Amgen's 6-[[[(S)-(3-fluoro-2-pyridinyl)[3-fluoro-4-(trifluoromethoxy)phenyl]methyl]amino]carbonyl]-3-pyridinecarboxylic acid (AMG 333) were evaluated in Phase I clinical trials and neither progressed further. For Amgen's trial of AMG 333, the results obtained evidenced adverse effects including feeling hot, paresthesia, dysesthesia, and dysgeusia (Fernandez-Carvajal, A., et al., Expert Opinion on Investigational Drugs, Volume 29, 2020-Issue 11). Similar adverse events were observed during Pfizer's trial of PF-05105679 at doses required for efficacy in a cold pressor test (Winchester, W. et al., Journal of Pharmacology and Experimental Therapeutics, Volume 351, 2014-Issue 2).

The present disclosure demonstrates that, in contrast to PF-05105679 and AMG 333, the TRPM8 inhibitor 4-({(4-cyclopropylisoquinolin-3-yl)[4-(trifluoromethoxy)benzyl] amino}sulfonyl)benzoic acid (also known as elismetrep) can be efficacious for treating migraine and other trigeminal pain disorders without the undesired side effects produced by other TRPM8 inhibitors, such as body temperature dysregulation, feeling hot, paresthesia, dysesthesia, and dysgeusia. Elismetrep is surprisingly more effective in migraine models than it is in body core temperature models, leading to a much larger therapeutic index and potential for treatment of migraine and other trigeminal pain disorders.

Definitions

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

The term "about" when referring to a number or a numerical range means that the number or numerical range referred to is an approximation within experimental variability (or within statistical experimental error), and thus the number or numerical range, in some instances, will vary between 1% and 15% of the stated number or numerical range. In some instances, "about" means within 10% of the stated number or numerical range.

The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

"Elismetrep" refers to the compound 4-({(4-cyclopropylisoquinolin-3-yl)[4-(trifluoromethoxy)benzyl] amino}sulfonyl)benzoic acid, pictured below:

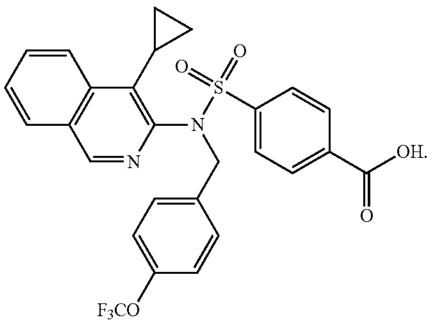 [SMILES: O=C(O)c1ccc(S(=O)(=O)N(Cc2ccc(OC(F)(F)F)cc2)c2ncc3ccccc3c2C2CC2)cc1]

The term "salt" or "pharmaceutically acceptable salt" refers to salts derived from a variety of organic and inorganic counter ions well known in the art. Pharmaceutically acceptable acid addition salts can be formed with inorganic acids and organic acids. Pharmaceutically acceptable base addition salts can be formed with inorganic and organic bases.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient.

The term "preventing" is art-recognized, and when used in relation to a condition, such as headache, is well understood in the art, and includes administration of a composition which reduces the frequency of, or delays the onset of, symptoms of a medical condition in a subject relative to a subject which does not receive the composition. Thus, prevention of headache includes, for example, reducing the number of patients suffering from headaches in a population of patients receiving a prophylactic treatment relative to an untreated control population. Prevention of a headache condition also includes, for example, reducing the number of diagnoses of the headache condition in a treated population versus an untreated control population, and/or delaying the onset of symptoms of the headache condition in a treated population versus an untreated control population. Prevention of a headache condition also includes, for example, reducing the severity of headache pain or most bothersome symptoms.

As used herein, the phrase "therapeutically effective amount," means the amount of a compound that, when administered to a patient for treating a disease, is sufficient to treat the disease or condition. The "therapeutically effective amount" will vary depending on the compound, the disease and its severity and the age, weight, adsorption, distribution, metabolism and excretion etc., of the patient to be treated.

As used herein, "treatment" or "treating" refers to an approach for obtaining beneficial or desired results with respect to a disease, disorder, or medical condition including, but not limited to, a therapeutic benefit. In certain embodiments, treatment or treating involves administering a compound or composition disclosed herein to a subject. A therapeutic benefit may include the eradication or amelioration of the underlying disorder being treated. For example, treating a headache disorder might include reducing the severity of headache pain or most bothersome symptoms.

As used herein, the term of "core body temperature" refers to the internal body temperature of a subject. Core body temperature can be measured using techniques known in the art. In some embodiments, invasive means are used, such as placing a temperature probe into the esophagus, pulmonary artery, or urinary bladder. In some embodiments, core body temperature is measured at a digestive organ. In some embodiments, core body temperature is measured at noninvasive sites, such as the rectum, oral cavity, axilla, temporal artery, or external auditory canal. In some embodiments, core body temperature is consistently measured at the same site, e.g., when evaluating the occurrence and/or extent of a decrease in core body temperature of a subject.

As used herein, the term "administer", "administered", "administration", or "to administer" refers to the step of giving (i.e. administering) a pharmaceutical composition to a subject, or alternatively a subject receiving a pharmaceutical composition. The pharmaceutical compositions disclosed herein can be locally administered by various methods. For example, intramuscular, intradermal, subcutaneous administration, intrathecal administration, intraperitoneal administration, topical (transdermal), instillation, and implantation (for example, of a slow-release device such as polymeric implant or miniosmotic pump) can all be appropriate routes of administration.

The terms "subject," "individual," and "patient" may be used interchangeably and refer to humans, as well as non-human mammals (e.g., non-human primates, canines, equines, felines, porcines, bovines, ungulates, lagomorphs, rodents, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for, a pathology to be prophylactically or therapeutically treated with a therapeutic protein described herein.

Methods of Use

As disclosed herein, elismetrep, being a TRPM8 antagonist, is useful in methods of treating or preventing diseases and conditions in a subject, wherein the disease or condition is mediated by TRPM8 activity. Activation of the trigeminovascular system resulting in pain is observed in disorders including migraine, headache disorders, cluster headache, trigeminal neuralgia, trigeminal neuropathy, and trigeminal autonomic cephalalgias. TRPM8 is expressed in the trigeminal ganglia and its activation has been shown to cause pain in some preclinical studies in rodents (Cephalalgia, 2015 May 5; 36(2): 185-193). Therefore, blocking of TRPM8 activation may be beneficial in disorders and diseases of the trigeminovascular system.

In particular aspects disclosed herein, elismetrep is useful for preventing or treating migraine and diseases of the trigeminovascular system. In some embodiments, the disease of the trigeminovascular system comprises orofacial pain, trigeminal neuralgia, trigeminal neuropathy, trigeminal autonomic cephalalgia, and dental pain. In some embodiments, elismetrep is useful for preventing or treating a pain disease or condition, migraine, a disease or condition of the trigeminovascular system, ischemia, irritable bowel syndrome, Raynaud's syndrome, neurodegeneration, fibromyalgia, stroke, itch, a psychiatric disorder, an inflammatory disorder, a hypersensitivity disorder, a urological disease or disorder, or a combination thereof. In some embodiments, elismetrep is useful for preventing or treating inflammatory pain, inflammatory hypersensitivity conditions, neuropathic pain, and cardiovascular disease aggravated by cold, including peripheral vascular disease, vascular hypertension, pulmonary hypertension, Raynaud's disease, and coronary artery disease.

Examples of inflammatory pain include pain due to a disease, condition, or a pain state including inflammatory bowel disease, irritable bowel syndrome, migraine, post operative pain, back pain, lower back pain, joint pain, abdominal pain, chest pain, visceral pain, labor, postmastectomy pain syndrome, menstrual pain, musculoskeletal diseases, skin diseases, toothache, osteoarthritis, rheumatoid arthritis, neurogenic bladder, interstitial cystitis, urinary tract infection, rhinitis, contact dermatitis/hypersensitivity, itch, eczema, pharyngitis, mucositis, enteritis, Raynaud's syndrome, cholecystitis, pancreatitis, endometriosis, sinus headache, tension headache, arachnoiditis, pyrosis, burn, sunburn, snake bite, venomous snake bite, spider bite, or insect sting.

One type of inflammatory pain is inflammatory hyperalgesia. Inflammatory hyperalgesia can be further distinguished as inflammatory somatic hyperalgesia or inflammatory visceral hyperalgesia. In some instances, inflammatory visceral hyperalgesia is characterized by the presence of an inflammatory hyperalgesic state, in which an enhanced visceral irritability exists. In some instances, inflammatory somatic hyperalgesia is characterized by the presence of an inflammatory hyperalgesic state in which a hypersensitivity to thermal, mechanical and/or chemical stimuli exists. Examples of inflammatory hyperalgesia include a disease, condition, or pain state including inflammation, osteoarthritis, rheumatoid arthritis, headaches, toothache, back pain, joint pain, abdominal pain, musculoskeletal diseases, post operative pain, neurogenic bladder, urinary incontinence, interstitial cystitis, urinary tract infection, cough, asthma, chronic obstructive pulmonary disease, rhinitis, skin diseases, contact dermatitis/hypersensitivity, itch, eczema, pharyngitis, enteritis, irritable bowel syndrome, Raynaud's syndrome, inflammatory bowel diseases including Crohn's Disease or ulcerative colitis, burn, sunburn, or insect sting.

Examples of an inflammatory hypersensitivity condition include urinary incontinence, benign prostatic hypertrophy, cough, asthma, rhinitis and nasal hypersensitivity, itch, contact dermatitis and/or dermal allergy, and chronic obstructive pulmonary disease.

Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, neuralgias (trigeminal neuralgia, glossopharyngeal neuralgia, postherpetic neuralgia and causalgia), lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paraesthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngeal neuralgia, migrainous neuralgia, idiopathic neuralgia, intercostal neuralgia, mammary neuralgia, Morton's neuralgia, nasociliary neuralgia, occipital neuralgia, red neuralgia, Sluder's neuralgia, sphenopalatine neuralgia, supraorbital neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain or neuralgia, pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

TRPM8 is highly expressed in sensory neurons of the trigeminal and dorsal root ganglia. In some embodiments, TRPM8 plays a role in headache disorders.

In some embodiments disclosed herein, elismetrep, or a pharmaceutically acceptable salt thereof, may therefore is useful for the treatment of a headache disorder. In some embodiments disclosed herein, elismetrep, or a pharmaceutically acceptable salt thereof, may therefore is useful for the treatment of migraine and other trigeminal pain disorders. In some embodiments, the headache disorder is selected from migraine, medication overuse headache, cluster headache, general headache, tension headache, caffeine headache, hormone headache, hemicrania continua, hypertension headache, rebound headache, post-traumatic headache, exertion headache, spinal headache, thunderclap headache, icepick headache, trigeminal neuralgia, orofacial pain (e.g., chronic orofacial pain), or a combination of two or more of these diseases or conditions. Non-limiting examples of said combinations include migraine and general headache, general headache and trigeminal neuralgia, and cluster headache and orofacial pain. In some embodiments, the headache disorder is selected from the group consisting of: migraine, medication overuse headache, cluster headache, general headache, trigeminal neuralgia, trigeminal neuropathy, trigeminal autonomic cephalalgia, and orofacial pain. In further embodiments, the disease or condition is migraine.

In some embodiments of the treatments disclosed herein, the subject is a mammal. In some embodiments, the subject is a human.

In one aspect, disclosed herein is a method for treating or preventing a disease or condition in a subject in need thereof, comprising administering to the subject a therapeutically effective amount of 4-({(4-cyclopropylisoquinolin-3-yl)[4-(trifluoromethoxy)benzyl]amino}sulfonyl)benzoic acid (elismetrep), or a pharmaceutically acceptable salt thereof, wherein the disease or condition is a pain disease or condition, ischemia, irritable bowel syndrome, Raynaud's syndrome, neurodegeneration, fibromyalgia, stroke, itch, a psychiatric disorder, an inflammatory disorder, anxiety, a urological disease or disorder, or a combination thereof.

In some embodiments, the disease or condition is a pain disease or condition. In some embodiments, the pain disease or condition is selected from the group consisting of acute pain, chronic pain, inflammatory pain, neuropathic pain, dental pain, postoperative pain, nerve injury, general headache, migraine, cluster headache, medication overuse headache, tension headache, hyperalgesia, allodynia, diabetic neuropathy pain, trigeminal neuralgia, trigeminal neuropathy, trigeminal autonomic cephalalgia, and orofacial pain.

In some embodiments, the disease or condition is selected from the group consisting of migraine, medication overuse headache, cluster headache, general headache, trigeminal neuralgia, trigeminal neuropathy, trigeminal autonomic cephalalgia, orofacial pain, and dental pain. In some embodiments, the disease or condition is selected from the group consisting of migraine, medication overuse headache, cluster headache, and general headache. In some embodiments, the disease or condition is migraine.

In one aspect, disclosed herein is a method for treating or preventing a disease or condition in a subject in need thereof, comprising administering to the subject a therapeutically effective amount of 4-({(4-cyclopropylisoquinolin-3-yl)[4-(trifluoromethoxy)benzyl]amino}sulfonyl)benzoic acid, or a pharmaceutically acceptable salt thereof, wherein the disease or condition is migraine or a trigeminal pain disease or condition.

In some embodiments, the disease or condition is selected from the group consisting of migraine, medication overuse headache, cluster headache, general headache, trigeminal neuralgia, trigeminal neuropathy, trigeminal autonomic cephalalgia, orofacial pain, and dental pain. In some embodiments, the disease or condition is selected from the group consisting of migraine, medication overuse headache, cluster headache, and general headache. In some embodiments, the disease or condition is migraine.

In one aspect disclosed herein, in some embodiments, is a method of treating or preventing a disease or condition in a human in need thereof, the method comprising orally administering to the human a therapeutically effective amount of 4-({(4-cyclopropylisoquinolin-3-yl)[4-(trifluoromethoxy)benzyl]amino}sulfonyl)benzoic acid (elismetrep), or a pharmaceutically acceptable salt thereof, wherein the disease or condition is migraine, medication overuse headache, cluster headache, general headache, or a combination thereof.

In the sensory nervous system, TRPM8 has a prominent role in the sensing of cold temperatures and maintaining core body temperature. In general, TRPM8 is a thermosensor that is activated by cool temperatures between 15 and 28° C. It also responds to chemical compounds like menthol, icilin, and eucalyptol, which create a cooling sensation. TRPM8-deficient mice have lower general body temperature, but are unable to regulate their core temperature. In one study, TRPM8-deficient mice received an injection of LPS which initially led to hypothermia which gradually shifted to a fever (Shiraki, C., et al., Brain, Behavior, & Immunity—Health, Volume 16, October 2021, 100291). Accordingly, any treatment targeting TRPM8 must take into account body temperature dysregulation as a potential side effect. Other side effects of TRPM8 inhibition include feeling hot, paresthesia, dysesthesia, and dysgeus.

In some embodiments as disclosed herein, a therapeutically effective dose for elismetrep for treating a disease or condition described herein (such as headache disorders, including migraine) does not induce an undesired side effect. In some embodiments, the side effect comprises body temperature dysregulation, feeling hot, paresthesia, dysesthesia, dysgeusia, or a combination thereof. In some embodiments, the side effect comprises feeling hot, paresthesia, dysesthesia, dysgeusia, or a combination thereof. In some instances, "paresthesia" refers to the sensation of tingling, burning, pricking or prickling, skin-crawling, itching, "pins and needles" or numbness on or just underneath the skin. In some instances, "dysesthesia" is the term for symptoms that disrupt how touch-based sensations are experienced; that is, the sense of touch can be unpleasant, unusual or painful. Similarly, "dysgeusia" refers to a taste disorder that causes an altered perception of taste, such as a persistent foul, salty, rancid, or metallic taste in the mouth.

In some embodiments as disclosed herein, a therapeutically effective dose for elismetrep for treating a disease or condition described herein does not induce body temperature dysregulation. In some embodiments as disclosed herein, a therapeutically effective dose for elismetrep for treating a disease or condition described herein does not induce feeling hot. In some embodiments as disclosed herein, a therapeutically effective dose for elismetrep for treating a disease or condition described herein does not induce paresthesia. In some embodiments as disclosed herein, a therapeutically effective dose for elismetrep for treating a disease or condition described herein does not induce dysgeus.

This is in contrast to the other known TRPM8 inhibitors which have been investigated in the clinic for treatment of pain, namely PF-05105679 and AMG 333. In studies of these compounds, undesired side effects, such as feeling hot, paresthesia, dysesthesia, dysgeusia, and general body temperature dysregulation led to discontinuation of the clinical trials.

In some embodiments, the ratio of minimal efficacious dose in a disease treatment model to a side effect model is referred to as the "therapeutic index" for elismetrep. In some specific embodiments disclosed herein, the minimal efficacious dose is determined in an in vivo rat migraine model, such as the acute isosorbide dinitrate (ISDN) model (see Example I). In some embodiments, the side effect is dysregulation of core body temperature. In some embodiments, the side effect comprises feeling hot, paresthesia, dysesthesia, dysgeusia, or a combination thereof. In some embodiments, the minimal dose required for causing a side effect is determined in an in vivo rat model, where core temperature is measured after administration of compound (see Example II). In some embodiments, the therapeutic index of elismetrep, or a pharmaceutically acceptable salt thereof, is at least 5:1, at least 10:1, at least 20:1, at least 30:1, at least 40:1, at least 50:1, at least 60:1, at least 70:1, at least 80:1, at least 90:1, at least 100:1, or more, wherein the therapeutic index is measured as the ratio of minimal dose for onset of an undesired side effect described herein: minimum dose needed for efficacy in treating or preventing the disease or condition. In some embodiments, the therapeutic index of elismetrep, or a pharmaceutically acceptable salt thereof, is at least 5:1, at least 10:1, at least 20:1, at least 30:1, at least 40:1, at least 50:1, at least 60:1, at least 70:1, at least 80:1, at least 90:1, at least 100:1, or more, wherein the therapeutic index is measured as the ratio of minimal dose for onset of a body temperature dysregulation effect:minimum dose needed for efficacy in treating or preventing the disease or condition. In some embodiments, the therapeutic index of elismetrep, or a pharmaceutically acceptable salt thereof, is at least 5:1, at least 10:1, at least 20:1, at least 30:1, at least 40:1, at least 50:1, at least 60:1, at least 70:1, at least 80:1, at least 90:1, at least 100:1, or more, wherein the therapeutic index is measured as the ratio of minimal dose which causes a change in core body temperature:minimum efficacious dose in an animal migraine model.

In some embodiments, the "therapeutic index" of elismetrep is a term used when describing the safety of elismetrep as determined in a human trial. For example, a difference in the percentage of patients achieving efficacy and those experiencing a side effect can be referred to as a therapeutic index.

In some embodiments described herein, efficacy is determined relative to placebo dosing. In some specific embodiments regarding migraine, for example, efficacy refers to an increased proportion of subjects achieving pain freedom (PF), freedom from the most bothersome symptom (MBS) associated with migraine, or pain relief (PR) two hours post-dosing of elismetrep relative to placebo. In some embodiments, efficacy refers to an increased proportion of subjects achieving PF; freedom from MBS; PR; freedom from photophobia, phonophobia, nausea; or freedom from another symptom of migraine two hours post-dosing of elismetrep relative to placebo. In some embodiments, efficacy refers to an increased proportion of subjects achieving PF; freedom from MBS; PR; freedom from photophobia, phonophobia, nausea; or freedom from another symptom of migraine from two to 24 hours post-dosing of elismetrep relative to placebo. In some embodiments, efficacy refers to an increased proportion of subjects achieving freedom from functional disability two hours post-dosing of elismetrep relative to placebo. In some embodiments, efficacy refers to decreasing the incidence of pain relapse in a subject post-dosing of elismetrep relative to placebo.

In some embodiments described herein, an observed side-effect post-dosing with elismetrep can be parethesia, feeling hot/feeling cold, dysgeusia, decreased body temperature, or dizziness. Side effects are also, in some embodiments, referred to as "adverse events" (AEs) or "treatment emergent adverse events" (TEAEs). TEAEs can be mild, moderate, or severe in intensity. In some specific embodiments described herein, in contrast to previous studies of TRPM8 inhibitors in the clinic, there are no serious TEAEs after dosing with elismetrep. In some specific embodiments, there are dose-dependent increases in the proportion of subjects reporting AEs. In some specific embodiments described herein, any AEs were of mild-moderate intensity.

In some specific embodiments described herein, there is a higher proportion of subject achieving efficacy than the proportion of subjects experiencing adverse events after dosing with elismetrep. In some embodiments, this represents a good therapeutic index for elismetrep. In some specific embodiments described herein, there is a higher proportion of subject achieving pain relief than the proportion of subjects experiencing adverse events after dosing with elismetrep. In some specific embodiments described herein, there is a higher proportion of subject achieving pain freedom than the proportion of subjects experiencing adverse events after dosing with elismetrep. In some specific embodiments described herein, there is a higher proportion of subject achieving freedom from the most bothersome symptom associated with migraine than the proportion of subjects experiencing adverse events after dosing with elismetrep.

Pharmaceutical Formulations

In some aspects, the present disclosure provides a pharmaceutical composition comprising elismetrep, or a pharmaceutically acceptable salt thereof, and at least one pharmaceutically acceptable excipient.

Elismetrep may be formulated in any suitable pharmaceutical formulation. A pharmaceutical formulation of the present disclosure typically contains an active ingredient (e.g., elismetrep), and one or more pharmaceutically acceptable excipients or carriers, including but not limited to: inert solid diluents and fillers, diluents, sterile aqueous solution and various organic solvents, permeation enhancers, antioxidants, solubilizers, and adjuvants. Preparations for such pharmaceutical composition are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999).

The amount of a therapeutic agent of the present disclosure will be dependent on the mammal being treated, the severity of the disorder or condition, the rate of administration, and the discretion of the prescribing physician. For example, a therapeutically effective amount of elismetrep, or a pharmaceutically acceptable salt thereof, includes a dose range from about 0.05 mg to about 100 mg in a regimen of about once a day, twice a day, three times a day, or four times a day for an average human. In specific embodiments herein, the therapeutically effective amount is less than 10 mg, less than 15 mg, less than 20 mg, or less than 25 mg; and the compound is orally administered once or twice per day. In some aspects, the therapeutically effective amount administered to the human is administered at a low enough dose to avoid unwanted side effects, such as temperature dysregulation effects, feeling hot, paresthesia, dysesthesia, dysgeusia, or a combination thereof. In some embodiments, the therapeutically effective amount of elismetrep, or a pharmaceutically acceptable salt thereof, is administered upon the onset of a migraine, or symptoms of a migraine. In some embodiments, the therapeutically effective amount of elismetrep, or a pharmaceutically acceptable salt thereof, is administered immediately upon the onset of a migraine, or symptoms of a migraine. In some embodiments, a therapeutically effective amount of elismetrep, or a pharmaceutically acceptable salt thereof, is a daily dose of less than 10 mg, less than 15 mg, less than 20 mg, or less than 25 mg. In some embodiments, a therapeutically effective amount of elismetrep, or a pharmaceutically acceptable salt thereof, is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, or about 25 mg. In some embodiments, a therapeutically effective amount of elismetrep, or a pharmaceutically acceptable salt thereof, is about 2 mg, about 5 mg, about 10 mg, or about 20 mg. In some embodiments, a therapeutically effective amount of elismetrep, or a pharmaceutically acceptable salt thereof, is about 10 mg or about 20 mg. In some embodiments, elismetrep, or a pharmaceutically acceptable salt thereof, is administered once daily or twice daily. In some embodiments, elismetrep, or a pharmaceutically acceptable salt thereof, is administered once daily upon the onset of a migraine, or symptoms of a migraine.

In one aspect, disclosed herein is a method of treating or preventing migraine in a human in need thereof, the method comprising orally administering to the human 4-({(4-cyclopropylisoquinolin-3-yl)[4-(trifluoromethoxy)benzyl]amino}sulfonyl)benzoic acid (elismetrep), or a pharmaceutically acceptable salt thereof, in a daily dose of less than 10 mg, less than 15 mg, less than 20 mg, or less than 25 mg. In some embodiments, a therapeutically effective amount of elismetrep, or a pharmaceutically acceptable salt thereof, is from 0.1 mg to 10 mg, 15 mg, 20 mg, or 25 mg. In some embodiments, a therapeutically effective amount of elismetrep, or a pharmaceutically acceptable salt thereof, is from 0.1 mg to 10 mg. In some embodiments, a therapeutically effective amount of elismetrep, or a pharmaceutically acceptable salt thereof, is from 0.1 mg to 15 mg. In some embodiments, a therapeutically effective amount of elismetrep, or a pharmaceutically acceptable salt thereof, is from 0.1 mg to 20 mg. In some embodiments, a therapeutically effective amount of elismetrep, or a pharmaceutically acceptable salt thereof, is from 0.1 mg to 25 mg. In some embodiments, a therapeutically effective amount of elismetrep, or a pharmaceutically acceptable salt thereof, is from 0.1 mg to 5 mg. In some embodiments, a therapeutically effective amount of elismetrep, or a pharmaceutically acceptable salt thereof, is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, or about 25 mg. In some embodiments, a therapeutically effective amount of elismetrep, or a pharmaceutically acceptable salt thereof, is about 2 mg, about 5 mg, about 10 mg, or about 20 mg. In some embodiments, a therapeutically effective amount of elismetrep, or a pharmaceutically acceptable salt thereof, is about 10 mg or about 20 mg. In some embodiments, a therapeutically effective amount of elismetrep, or a pharmaceutically acceptable salt thereof, is about 2 mg, about 5 mg, about 10 mg, or about 20 mg. In some embodiments, a therapeutically effective amount of elismetrep, or a pharmaceutically acceptable salt thereof, is about 10 mg or about 20 mg.

In some embodiments, elismetrep as described herein is used in the preparation of medicaments for the prevention or treatment of diseases or conditions.

In prophylactic applications, compositions containing elismetrep as described herein are administered to a patient susceptible to or otherwise at risk of a disorder or condition (e.g. a headache disorder). Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

A pharmaceutical formulation of the present disclosure may be administered to the subject using different administration routes, including oral, transmucosal, topical, transdermal, inhalation, intravenous, subcutaneous, intradermal, intramuscular, intra-articular, perineural, intraventricular, intravenous, intraperitoneal, intranasal, and intraocular.

EXAMPLES

The following examples are illustrative and non-limiting to the scope of the compositions, devices, and methods disclosed herein.

Example 1. In Vivo Assay of Compounds for Determining Efficacy in a Rat Migraine Model An acute isosorbide dinitrate (ISDN) model was used to assess migraine efficacy in rats. (For review see: Dallel R, Cephalalgia. 2018; 38 (4): 776-785).

Briefly, male Sprague Dawley rats, 8-weeks old (Charles River Laboratories), were pair-housed in a 12-h light cycle room upon facility arrival and left to acclimate for a minimum of 72 h. Animals were provided standard rodent chow (PicoLab Rodent Diet, 5053) and water ad libitum. Following the acclimation period, rats underwent a single behavioral testing apparatus acclimation. Rats were left to freely move and habituate for a minimum of 20 min. The testing apparatus used was a Multiple Configuration Animal Enclosure (Ugo Basile, 37000-007) placed on a self-standing table with a mesh-perforated bottom.

Periorbital threshold was measured using the up-down method (Chaplan, S. R., et al., J Neurosci Methods, 1994 July; 53 (1): 55-63), in which von Frey filaments (Ugo Basile, 37450-275) of increasing forces (0.4-15 g) were applied to the periorbital region until an application of a filament evoked a response, typically indicated by a rapid withdrawal response or paw swipe to the periorbital region. Once a response was observed, four more readings were obtained following the first change of direction to determine the withdrawal threshold close to 50%. The 50% threshold was then calculated using the following formula: 50% threshold (g)=10 (X+kd)/104, where X=the value, in log units, of the final von Frey filament, k=tabular value for the response pattern, and d=the average increment, in log units, between von Frey filaments.

Following acclimation, a baseline assessment was performed, and rats were then randomized into balanced treatment groups using baseline periorbital threshold measurements. On the day of the experiment, rats (n=12/group) were weighed and administered vehicle (0.25% methyl cellulose, 5% Tween 80, 0.02% sodium dodecyl sulfate (SDS) in Hanks' Buffered Salt Solution with Ca2+ and Mg2+), 10 mg/kg sumatriptan as a positive control (2 mg/mL in vehicle; Ambeed, A260899-1 g) or test compound (5 mL/kg in vehicle). Thirty minutes post-compound dosing, rats were administered 20 mg/kg ISDN (4 mg/mL in 1:9 DMSO and 20% aqueous 2-hydroxypropyl-β-cyclodextrin; Medchem Express, HY-B1409) by intraperitoneal injection.

Approximately 70 min post-compound dosing, animals were placed in the behavioral testing apparatus and allowed to habituate to individual enclosures. Von Frey measurements were then recorded at 90 and 120 minutes post-compound dosing. Upon final measurement, rats were immediately euthanized via CO2 asphyxiation followed by exsanguination. Blood was collected in lithium-heparin serum-separating tubes (BD, 365985) and processed for serum collection. Serum samples were then stored at −80° C.

For analysis, von Frey measurement was capped at 10 g, which was considered the baseline periorbital threshold for SD rats. All values over 10 g were recorded as 10 g. Statistical analysis was performed using GraphPad Prism using two-way ANOVA followed by a Dunnett post-hoc test. Migraine efficacy is defined as the dose of a compound at which there is a significant difference from vehicle treatment in periorbital threshold at a given timepoint. Adjusted p values are shown for the lowest dose to achieve efficacy at either timepoint.

Dose response was measured for each of the TRPM8 inhibitors elismetrep, AMG 333, and PF-05105679. The minimum dose required for efficacy for elismetrep is 0.03 mg/kg (adjusted p value for 60 min timepoint=0.0505; adjusted p value for 90 min timepoint=0.0017); the minimum dose required for efficacy for AMG 333 is 1 mg/kg (adjusted p value for 60 min timepoint=0.5453; adjusted p value for 90 min timepoint=0.0193); and the minimum dose required for efficacy for PF-05105679 is 10 mg/kg (adjusted p value for 60 min timepoint=0.0042; adjusted p value for 90 min timepoint=0.2492).

Example 2. In Vivo Assay of Compounds for Determining Effects on Rat Core Temperature Briefly, male Sprague Dawley rats, 5-weeks old (Charles River Laboratories), were pair-housed in a 12-h light cycle room upon facility arrival and left to acclimate for a minimum of 72 h. Animals were provided standard rodent chow (PicoLab Rodent Diet, 5053) and water ad libitum. Following the acclimation period, temperature transponders (Avidity Science IPT-300) loaded into a disposable needle were implanted subcutaneously four days before experiment day. The implantation site was monitored daily after implantation. Temperature was measured using a wireless reader system (Avidity Science DAS-8027) that automatically scans implanted temperature transponders.

Rats are used one week after implantation. On the day of the experiment, rats (n=6/group) were weighed and baseline assessment performed for randomizing rats into balanced treatment groups. After sorting, rats were dosed via oral gavage with vehicle (0.25% methyl cellulose, 5% Tween 80, 0.02% sodium dodecyl sulfate (SDS) in Hanks' Buffered Salt Solution with Ca2+ and Mg2+) or test compound (5 mL/kg in vehicle). Temperatures were recorded at 0.5, 1.0, 1.5, 2.0, 4.0, and 6.0 hr post dosing.

The effect on core temperature was calculated by normalizing individual temperature points to their respective baseline values. Area under the curve (AUC) was calculated from the temperature change time course from 0 to 2 hr using the largest mean temperature change value as baseline. A one-way ANOVA was performed comparing the AUC of the test compound groups to the vehicle.

Dose response was measured for each of the TRPM8 inhibitors elismetrep, AMG 333, and PF-05105679. The minimum dose required for causing an effect on core temperature for elismetrep is 6 mg/kg (adjusted p value for 2 hr timepoint=0.0109, all other timepoints not significant (ns)); the minimum dose required for causing an effect on core temperature for AMG 333 is from 3 mg/kg (adjusted p value for 1.5 hr timepoint=0.0220, all other timepoints ns); and the minimum dose required for causing an effect on core temperature for PF-05105679 is from 60 mg/kg (adjusted p value for 1.5 hr timepoint=0.0369; for 2 hr timepoint=0.0060, all other timepoints ns).

Nitric oxide donors including nitroglycerin and isosorbite dinitrate (ISDN), as used in this example, reliably trigger migraines in migraineurs (Cephalalgia, 2020 Mar. 12; 40(8): 828-841). In rodents, administration of nitric oxide donors results in activation of the trigeminovascular system, facial allodynia and spontaneous pain (Neurobiology of Pain, 12 (2022), 100105). Nitroglycerin/ISDN administration in rodents is therefore a model of migraine and other disorders of the trigeminovascular system.

As demonstrated in the examples above, elismetrep demonstrates a unique left-shifting of potency in the migraine efficacy model that is not seen with other clinically relevant TRPM8 antagonists. The results are summarized in the table below.

TABLE 1

Left-Shift in Efficacy for Migraine vs Core Temperature is Unique to Elismetrep

| TRPM8 Antagonist | Minimal Dose for Efficacy (mg/kg) Migraine | Core Temperature | Minimal Dose Ratio (Core Temp/ Migraine) |
|---|---|---|---|
| Elismetrep | 0.03 | 6 | 200× |
| AMG 333 | 1 | 3 | 3× |
| PF-05105679 | 10 | 60 | 6× |

Accordingly, elismetrep is uniquely positioned to be a treatment for migraine and other disorders of the trigeminovascular system without the undesired side effects which led to the clinical failures of AMG 333 and PF-05105679.

Example 3: a Randomized, Double-Blind, Placebo-Controlled Dose-Finding Study of Elismetrep in the Treatment of Acute Migraine A non-limiting example of a clinical trial of elismetrep in humans is described below.

Purpose

This was a multi-center, randomized, double-blind, placebo-controlled, parallel-group study to evaluate the safety, tolerability, and efficacy of various doses of elismetrep in the treatment of patients with an acute migraine attack.

Study Design

Eligible subjects had an established diagnosis of migraine for at least one year by IHS criteria and were experiencing 2-10 headaches/month. 431 subjects were randomized in a 2:1:2:2:1 ratio to one of the following treatment groups: placebo, 2 mg, 5 mg, 10 mg, or 20 mg of elismetrep. Randomization was stratified according to use of background prophylactic medications for migraine (yes/no). Subjects treated a single migraine attack of moderate-severe intensity.

Subjects used an electronic diary (eDiary) to record migraine-related information. Upon experiencing a potentially qualifying migraine headache, subjects log in and answer questions designed to ascertain whether migraine headache is qualifying according to the criteria listed below and whether medications specifically prohibited 48 h prior to a qualifying migraine have been taken. During the 48 hours following the dose of study medication, patients record various measures in an eDiary at specified time intervals. These measures include subjective assessments of pain severity, presence or absence of migraine-associated symptoms, degree of functional disability, use of rescue medication (yes/no), and the onset of the first moderate or severe headache recurrence (if any).

The patients were instructed to take their study medication, as an outpatient. The patients were instructed to treat a migraine headache if the following conditions are met:

The migraine headache severity is moderate or severe (Grade 2 or 3).

The migraine headache started less than four hours ago.

The migraine headache is a new headache that has not been previously treated and is not a recurrence of a previous migraine headache (at least 48 hours must have elapsed since the complete termination of their last attack (pain and all associated symptoms)).

No other migraine headache or headache has occurred in the previous 48 hours.

The migraine headache is not already resolving on its own.

Prohibited medication has not been taken within the last 48 hours (any triptan, any ergot derivative, any opiate, any other form of analgesic, any non-steroidal anti-inflammatory agent, any antiemetic agent, any CGRP antagonist approved and used for acute migraine treatment (ubrogepant and zavegepant, and rimegepant), any ditan).

Subjects took study medication after answering diary questions about their current pain and symptoms and after identifying their currently most bothersome, migraine associated, symptom (phonophobia, photophobia or nausea).

Study Objectives

Primary Objective: To evaluate the efficacy of a range of dose levels of elismetrep compared with placebo in the acute treatment of migraine as measured by pain freedom (PF) at two hours post dose.

Secondary Objectives: To evaluate the efficacy of a range of dose levels of elismetrep compared to placebo on freedom from the most bothersome symptom (MBS), associated with migraine, at two hours post dose. To evaluate the efficacy of a range of dose levels of elismetrep compared to placebo on pain relief (PR) at 2 hours post-dose. To evaluate the efficacy of a range of dose levels of elismetrep compared to placebo on freedom from photophobia at 2 hours post-dose. To evaluate the efficacy of a range of dose levels of elismetrep compared to placebo on freedom from phonophobia at 2 hours post-dose. To evaluate the efficacy of a range of dose levels of elismetrep compared to placebo on freedom from nausea at 2 hours post-dose. To evaluate the efficacy of a range of dose levels of elismetrep compared to placebo on the probability of requiring rescue medication within 24 hours of initial treatment. To evaluate the efficacy of a range of dose levels of elismetrep compared to placebo on sustained pain freedom from 2 to 24 hours post-dose. To evaluate the efficacy of a range of dose levels of elismetrep compared to placebo on sustained pain relief from 2 to 24 hours post-dose. To evaluate the efficacy of a range of dose levels of elismetrep compared to placebo on sustained pain freedom from 2 to 48 hours post-dose. To evaluate the efficacy of a range of dose levels of elismetrep compared to placebo on sustained pain relief from 2 to 48 hours post-dose. To evaluate the safety and tolerability of various doses of elismetrep in the treatment of acute migraine.

Exploratory Objectives: To evaluate the efficacy of a range of dose levels of elismetrep compared to placebo on freedom from functional disability at 2 hours post dose according to the Functional Disability scale for subjects who reported any level of disability at the migraine baseline. To evaluate the efficacy of a range of dose levels of elismetrep compared to placebo for the incidence of pain relapse from 2 to 48 hours post-dose.

Results 431 subjects were randomized and 398 treated a qualifying migraine. Mean age was 45.8 years, 86.9% were female, 35% were on prophylactic medications, and 31% were resistant to triptans.

Primary Objective: In the primary analysis only using efficacy data captured in an electronic diary, 9.1% of subjects in the placebo group and 17.6% of subjects in the 20 mg group were PF at 2 h. In a prespecified analysis including 2 h PF data that was reported by subjects but was missing from the e-diary, 2 h PF was reported in 9.1% of participants in the placebo group vs 19.6% in the 20 mg group.

Secondary Objectives: Freedom from MBS at 2 h was reported in 24.2% in the placebo group vs 27.3%, 40.0%, 32.2%, and 38.3% in the 2 mg, 5 mg, 10 mg, and 20 mg group, respectively. PR at 2 h was reported by 42.4% in the placebo group vs 56.9%, 55.4%, 52.1%, and 58.8% in the 2 mg, 5 mg, 10 mg, and 20 mg group, respectively.

Safety: There were no serious adverse events. There are five non-important identified risks: (1) paresthesia, (2) feeling hot/feeling cold, (3) dysgeusia, (4) decreased body temperature, and (5) dizziness. The incidence of paresthesia related AEs and AEs related to feeling hot/cold increased with dose. Most of these AEs were mild in intensity. Dysgeusia, dizziness, and decreased body temperature-related AEs were not commonly reported in this study. A summary of the most common AEs is provided in Table 2.

TABLE 2

| Dose | Placebo (N = 104) n(%) | 2 mg (N = 51) n(%) | 5 mg (N = 101) n(%) | 10 mg (N = 97) n(%) | 20 mg (N = 51) n(%) |
|---|---|---|---|---|---|
| Subjects with at least one paresthesia related TEAE | 0 | 0 | 1 (1.0) | 9 (9.3) | 9 (17.6) |
| Subjects with at least one feeling hot/cold related TEAE | 1 (1.0) | 0 | 0 | 4 (4.1) | 8 (15.7) |

Results

At each dose, a higher proportion of subjects achieved at least one efficacy endpoint than the proportion of subjects which experienced at least one TEAE.

For example, as seen in Table 3, the proportion of subjects achieving pain relief is significantly higher than the proportion of subjects experiencing a TEAE.

TABLE 3

| Dose | 2 h Pain Relief | TEAE: Paresthesia | TEAE: Feeling hot/cold |
|---|---|---|---|
| Placebo | 42.4% | 0% | 1% |
| 2 mg | 56.9% | 0% | 0% |
| 5 mg | 55.4% | 1% | 0% |
| 10 mg | 52.1% | 9.3% | 4.1% |
| 20 mg | 58.8 | 17.6% | 15.7% |

This data indicates that elismetrep possesses a measurable therapeutic index and that it is safe and effective in acute migraine.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating or preventing migraine in a human, the method comprising orally administering to the human in need thereof a therapeutically effective amount of 4-({(4-cyclopropylisoquinolin-3-yl)[4-(trifluoromethoxy)benzyl]amino}sulfonyl)benzoic acid, or a pharmaceutically acceptable salt thereof; wherein the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof, is an amount which provides efficacy but does not produce a severe treatment-emergent adverse event (TEAE); wherein efficacy refers to achieving pain freedom, freedom from the most bothersome symptom associated with migraine, or pain relief two hours post-dosing of 4-({(4-cyclopropylisoquinolin-3-y1)[4-(trifluoromethoxy)benzyl]amino}sulfonyl)benzoic acid, or a pharmaceutically acceptable salt thereof; and wherein the severe TEAE comprises feeling hot, paresthesia, dysesthesia, dysgeusia, or a combination thereof.

2. The method of claim 1, wherein the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof, is from 0.1 mg to 25 mg.

3. The method of claim 1, wherein the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof, is about 2 mg, about 5 mg, about 10 mg, or about 20 mg.

4. The method claim 1, wherein the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof, is about 10 mg or about 20 mg.

5. The method of claim 1, wherein the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof, is about 2 mg.

6. The method of claim 1, wherein the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof, is about 5 mg.

7. The method of claim 1, wherein the therapeutically effective amount of 4-({(4-cyclopropylisoquinolin-3-yl)[4-(trifluoromethoxy)benzyl]amino}sulfonyl)benzoic acid, or a pharmaceutically acceptable salt thereof, is about 10 mg.

8. The method of claim 1, wherein the therapeutically effective amount of 4-({(4-cyclopropylisoquinolin-3-yl)[4-

(trifluoromethoxy)benzyl]amino}sulfonyl)benzoic acid, or a pharmaceutically acceptable salt thereof, is about 20 mg.

9. The method of claim 1, wherein the 4-({(4-cyclopropylisoquinolin-3-yl)[4-(trifluoromethoxy)benzyl]amino}sulfonyl)benzoic acid, or a pharmaceutically acceptable salt thereof, is administered upon sensing the onset of a migraine.

10. The method of claim 1, wherein the 4-({(4-cyclopropylisoquinolin-3-yl)[4-(trifluoromethoxy)benzyl]amino}sulfonyl)benzoic acid, or a pharmaceutically acceptable salt thereof, is administered daily.

11. The method of claim 1, wherein the 4-({(4-cyclopropylisoquinolin-3-yl)[4-(trifluoromethoxy)benzyl]amino}sulfonyl)benzoic acid, or a pharmaceutically acceptable salt thereof, is administered once daily upon sensing the onset of a migraine.

12. The method of claim 1, wherein the migraine is acute migraine.

13. The method of claim 1, wherein the 4-({(4-cyclopropylisoquinolin-3-yl)[4-(trifluoromethoxy)benzyl]amino}sulfonyl)benzoic acid, or a pharmaceutically acceptable salt thereof, is 4-({(4-cyclopropylisoquinolin-3-yl)[4-(trifluoromethoxy)benzyl]amino}sulfonyl) benzoic acid.

* * * * *